United States Patent [19]

Etter et al.

[11] Patent Number: 4,794,131
[45] Date of Patent: Dec. 27, 1988

[54] PHOTO-PRODUCT ENERGY BARRIER COMPOSITION

[75] Inventors: Robert M. Etter; Phillip J. Neumiller, both of Racine County, Wis.

[73] Assignee: S. C. Johnson & Son, Inc., Racine, Wis.

[21] Appl. No.: 3,350

[22] Filed: Jan. 14, 1987

[51] Int. Cl.[4] .............................................. C08F 12/48
[52] U.S. Cl. ................................... 522/173; 522/178; 528/126; 528/128; 204/157.75
[58] Field of Search ............... 522/173, 178; 528/126, 528/128; 204/157.75

[56] References Cited

U.S. PATENT DOCUMENTS

| | | | |
|---|---|---|---|
| 1,962,132 | 6/1934 | Bradshaw | 106/173.1 |
| 2,639,290 | 5/1953 | Mahler | 556/110 |
| 2,686,812 | 8/1954 | Wynn et al. | 568/322 |
| 2,693,492 | 11/1954 | Hoch | 568/322 |
| 2,773,778 | 12/1956 | Hoch et al. | 252/589 |
| 2,876,210 | 3/1959 | Wynn et al. | 524/337 |
| 2,989,416 | 6/1961 | Standish | 524/241 |
| 3,043,709 | 7/1962 | Amborski | 428/216 |
| 3,049,443 | 8/1962 | Coleman | 8/527 |
| 3,098,863 | 7/1963 | Dassauer | 524/328 |
| 3,100,716 | 8/1963 | Kibler et al. | 106/187 |
| 3,206,428 | 9/1965 | Stanley | 260/45.9 |
| 3,216,969 | 11/1965 | Cyba | 524/204 |
| 3,296,191 | 1/1967 | Smallwood et al. | 524/328 |
| 3,361,709 | 1/1968 | Brown et al. | 524/328 |
| 3,413,263 | 11/1968 | Strobel et al. | 524/328 |
| 3,448,133 | 6/1969 | Strobel et al. | 556/150 |
| 3,460,960 | 8/1969 | Francel et al. | 428/336 |
| 3,464,953 | 9/1969 | Newland | 524/202 |
| 3,616,367 | 10/1971 | Zunker | 522/21 |
| 3,642,690 | 2/1972 | Mills | 524/100 |
| 3,755,450 | 8/1973 | Anderson et al. | 568/304 |
| 3,772,354 | 11/1974 | Fredricks et al. | 556/45 |
| 3,786,021 | 1/1974 | Mathis et al. | 524/204 |
| 3,871,901 | 3/1975 | Carlsson | 366/222 |
| 3,997,464 | 12/1976 | Tucker | 252/588 |
| 3,998,752 | 12/1976 | Haacke | 252/587 |
| 4,029,684 | 6/1977 | Avar et al. | 556/150 |
| 4,097,454 | 6/1978 | Tozzi et al. | 524/302 |
| 4,228,066 | 10/1980 | Johnson | 260/45.75 |

OTHER PUBLICATIONS

BASF Wyandotte Corporation Technical Data, "Unimal UV Absorbers, for Cosmetics, Plastics, Coatings, Textiles."

*Primary Examiner*—John C. Bleutge
*Assistant Examiner*—David Buttner

[57] ABSTRACT

This invention relates to photo-product compositions, and a process for making those compositions, comprising the reactant mixture formed by contacting: 2,2',4,4'-tetrahydroxybenzophenone, with (1) ammonium hydroxide and optionally a trace amount of at least one metal, or (2) ammonium hydroxide and at least one metal salt, or (3) at least one metal salt and at least one amine, or (4) ammonium hydroxide, at least one metal salt and at least one amine; in a suitable solvent, wherein a photo-product is formed upon exposure of this reactant mixture to light in the presence of an oxygen source.

67 Claims, 8 Drawing Sheets

PHOTO-PRODUCT ENERGY BARRIER COMPOSITION

The present invention relates to photo-product compositions, and processes for making those compositions, which significantly reduce the transmission of electromagnetic radiation, specifically in the infrared and ultraviolet range. More particularly, it relates to photo-product compositions, and processes for making those compositions, employing a substituted benzophenone reaction product which is exposed to light in the presence of an oxygen source.

It has long been desired to provide a product and coating film which provides an effective screen against ultraviolet and infrared radiation. Such a film can be applied to windows, painted surfaces, eyeglasses, fabrics and other substrates to protect them and their users from such radiation. Conventional films typically lack the desired absorption and adherency characteristics.

Benzophenones and substituted benzophenones are well known as ultraviolet light absorbers. See for example, BASF Wyandotte Corporation's Technical Data entitled "UVINUL UV Absorbers, For Cosmetics, Plastics, Coatings, Textiles", which discloses numerous substituted benzophenones, and 2,2',4,4'-tetrahydroxybenzophenone in particular, as useful absorbers of ultraviolet light for a variety of applications. Additionally, Smallwood et al., U.S. Pat. No. 3,296,191, discloses that thermally-produced nickel or cobalt derivatives of specified hydroxybenzophenones, which do not include 2,2,4,4'-tetrahydroxybenzophenone, are useful as light and heat stabilizers for polypropylenes. The disclosed benzophenones are 2,2'-dihydroxy-4-alkoxybenzophenones with $C_6$–$C_{20}$ alkyl radicals being required for effective stabilization. Additionally, the coordination complex contains no more than about one mole of metal for every two moles of benzophenone.

U.S. Pat. No. 2,989,416 to Standish, however, states that these materials, in general, are not entirely satisfactory because of the difficulty in applying them to surfaces and the relative ease by which they are washed from such surfaces. Standish addresses such problems by reacting certain ortho-hydroxyl substituted benzophenones, with a trivalent metal, either chromium or aluminum, in molar ratios of benzophenone to metal ranging from 1:0.5 to 1:10 to form water-soluble Werner complexes that absorb longer wavelength ultraviolet radiation. Additionally, the Standish product is a thermally-produced compound, not a composition produced by a photoreaction.

Accordingly, it is an object of this invention to provide a photo-product energy barrier that significantly reduces the transmission of electromagnetic radiation.

More specifically, it is an object of this invention to provide an energy barrier composition that significantly reduces the transmission of electromagnetic radiation by reflecting infrared radiation in the range of about 800 to 15,000 nanometers and absorbing ultraviolet radiation in the range of 200 to 400 nanometers.

Still more specifically, it is an object of this invention to provide a composition that strongly adheres to many surfaces, including plastic, wood, glass, metal, synthetic fibers, polymers and even Teflon ®, a trademark of Du Pont.

These and additional objectives are shown from the description below.

SUMMARY OF THE INVENTION

In one embodiment, this invention consists of a process for making a photo-product intermediate composition suitable for providing a photo-product upon exposure to light in the presence of an oxygen source comprising contacting: (a) 2,2',4,4'-tetrahydroxybenzophenone; (b) ammonium hydroxide; and (c) optionally a trace amount of at least one metal; in a solvent. ("Intermediate Reaction Process I").

"Intermediate Reaction Process II" is a related process comprising contacting: (a) 2,2',4,4'-tetrahydroxybenzophenone; (b) ammonium hydroxide; and (c) at least one metal salt; in a solvent.

"Intermediate Reaction process III" is also related and comprises contacting: (a) 2,2',4,4'-tetrahydroxybenzophenone; (b) at least one metal salt; and (c) at least one amine; in a solvent.

"Intermediate Reaction Process IV" comprises contacting: (a) 2,2',4,4'-tetra-hydroxybenzophenone; (b) ammonium hydroxide; (c) at least one metal salt; and (d) at least one amine; in a solvent.

In other embodiments, this invention relates to a process for making a photo-product composition comprising contacting the ingredients of one of the four above-noted intermediate compositions to form a reactant mixture, and exposing this reactant mixture to light in the presence of an oxygen source. ("Reaction Processes I-IV").

In still another embodiment, this invention consists of a photo-product intermediate composition suitable for providing a photo-product upon exposure to light in the presence of an oxygen source comprising: (a) 2,2',4,4'-tetrahydroxybenzophenone; (b) ammonium hydroxide; and (c) optionally a trace amount of at least one metal; in a solvent. ("Intermediate Reaction Product I").

Intermediate Reaction Product II is also a composition suitable for providing a photo-product upon exposure to light in the presence of an oxygen source comprising: (a) 2,2',4,4'-tetrahydroxybenzophenone; (b) ammonium hydroxide; and (c) at least one metal salt; in a solvent.

Intermediate Reaction Product III is a composition comprising: (a) 2,2',4,4'-tetrahydroxybenzophenone; (b) at least one metal salt; and (c) at least one amine; in a solvent.

A photo-product intermediate composition comprising: (a) 2,2,',4,4'-tetrahydroxybenzophenone; (b) ammonium hydroxide; (c) at least one metal salt; and (d) at least one amine; in a solvent, is "Intermediate Reaction Product IV".

In still other embodiments, this invention relates to photo-product compositions formed by employing one of the Intermediate Reaction Products I-IV.

It has been surprisingly found that 2,2',4,4'-tetrahydroxybenzophenone (THBP) in combination with: (1) ammonium hydroxide, or (2) ammonium hydroxide and at least one metal salt, or (3) at least one metal salt and at least one amine, or (4) ammonium hydroxide, at least one metal salt and at least one amine; in a suitable solvent, produces a photo-product upon exposure to light in the presence of oxygen. This photo-product significantly reduces the transmission of electromagnetic radiation by reflecting infrared radiation in the range of about 800 to 15,000 nanometers and absorbing ultraviolet radiation in the range of about 200 to 400 nanometers.

It has been additionally surprisingly found that the photo-product compositions of this invention tenaciously adhere to many substrates, including plastic, wood, glass, metal, synthetic fibers, polymers, and even Teflon ®, and are insoluble in water and many organic solvents and therefore cannot be routinely removed from these substrates once applied.

DETAILED DESCRIPTION OF THE INVENTION

Figure 1:
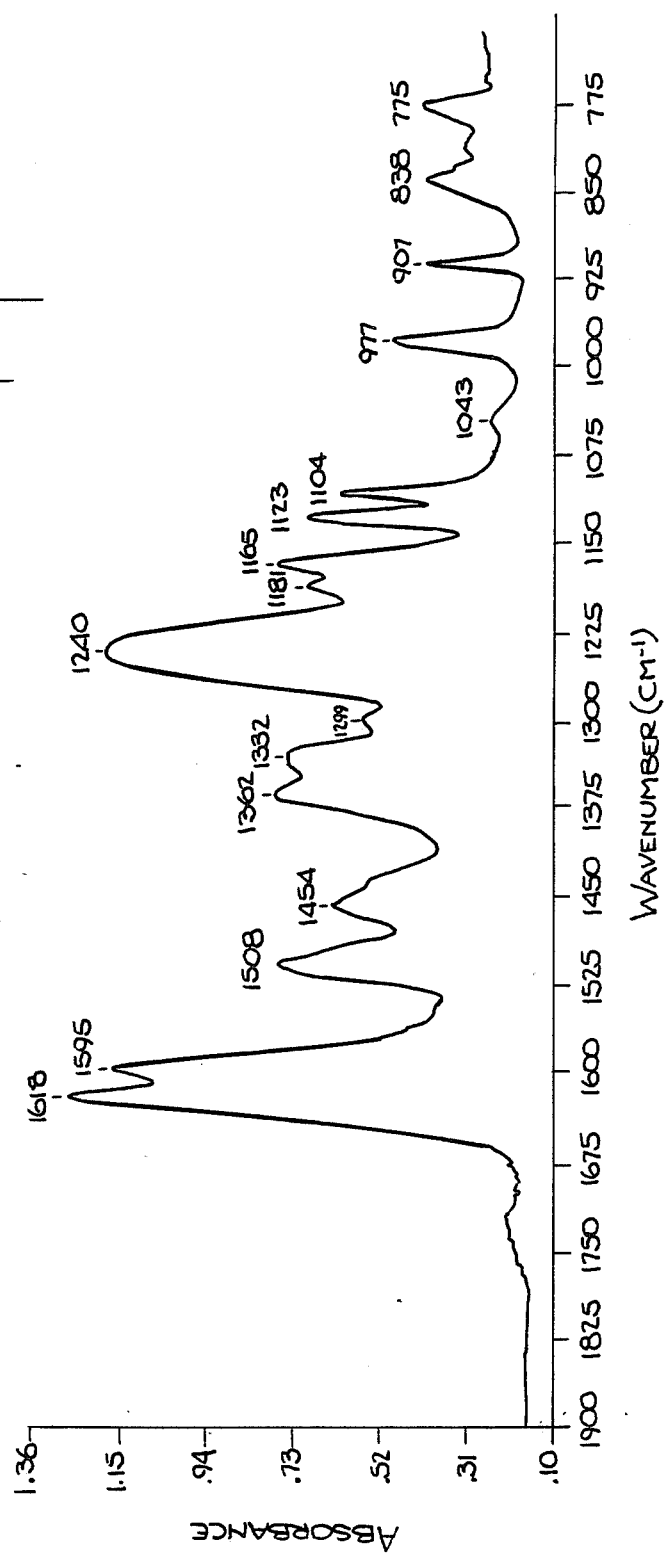
FIG. 1 is the infrared absorption spectrum for an Intermediate Reaction Product I composition, prior to light exposure, as described herein.

In one embodiment, the invention consists of a process for making a photo-product intermediate composition suitable for providing a photo-product upon exposure to light in the presence of an oxygen source comprising contacting: (a) 2,2',4,4'-tetrahydroxybenzophenone; (b) ammonium hydroxide; and (c) optionally a trace amount of at least one metal; in a solvent.

The invention also relates to a process for making a photo-product, which is formed by exposing the above reactant mixture to light in the presence of an oxygen source. ("Reaction Process I"). Additionally, the photo-product intermediate composition and the photo-product composition ("Reaction Product I") made by the above processes are within the scope of this invention.

In this and the other, more preferred, embodiments of this invention, the benzophenone found best to entirely meet the objectives of this invention and provide a photo-product is 2,2'4,4'-tetrahydroxybenzophenone (THBP). Other benzophenones that do not yield the present photo-product composition include: 2,2'-dihydroxybenzophenone; 2,2'-dihydroxy-4,4' dimethoxybenzophenone; 4,4'-dihydroxybenzophenone; and 2,4'-dihydroxybenzophenone. These particular benzophenones were tested in a composition of Reaction Product IV and found to give various precipitants without producing a photo-product of this invention.

Additionally, certain sources of ammonium ion ($NH_4+$) and hydroxyl ion (—OH) other than ammonium hydroxide have not proven effective in producing the photo-product compositions of this invention. For example, benzyltrimethyl ammonium hydroxide, tetramethyl ammonium hydroxide, ammonium bromide and ammonium acetate, all failed to produce the requisite photo-product when utilized as substitutes for ammonium hydroxide in a Reaction Product IV composition.

However, in a Reaction Product I formula, a metal need not be added to the mixture of reactants. X-ray analysis has shown that when combining THBP and ammonium hydroxide in the presence of a solvent, trace amounts of metals, in particular, zinc, are typically present as contaminants.

It is believed that the trace amounts of metal assist in forming and stabilizing the reaction product. In the other Reaction Product formulas, at least one metal salt is intentionally added to the mixture of reactants. Useful metals are provided hereafter in connection with the discussion of Reaction Process and Product II.

The concentration of THBP and ammonium hydroxide utilized in accordance with this aspect of the invention varies from a molar ratio of 1:1 to about 20:1, with a molar ratio of 18 moles of THBP to about 5 moles of ammonium hydroxide being preferred.

The reaction is typically carried out at room temperature (approximately 22° C.). The reaction temperature is not critical, and the addition of heat is not necessary, nor is it a limiting factor in the photo-product reaction. However, with some of the other reaction product formulas a heat treatment may be necessary to promote the solubilization of the reactants.

The photo-reaction is carried out in the presence of light, such as sunlight or artificially produced ultraviolet radiation in the range of about 200 to 400 nanometers, with about 340 to 360 nanometers being preferred. The more intense the light, particularly light in the 340 to 360 nanometer range, the more rapid the formation of the photo-product. Artificial light in this range, e.g., light produced by a mercury arc lamp, (medium pressure immersion lamp Canrad-Hanovia 100 and 400 watt), enhances the rate of photo-product formation and can, under certain circumstances, provide a visible film in a few hours. Additionally, this photo-product film adheres less tenaciously to various substrates as compared to Reaction Products II and IV. Reaction Product I is also dissolved by dimethyl formamide.

A visible film of Reaction Product I forms slowly on the sides of a glass vial or on a glass substrate. While the photo-product can be detected almost instantly upon mixing the reactants under the proper conditions, it usually takes between about 2 and 3 days of exposure of these Reaction Product I reactants to direct sunlight before a film becomes noticeable to the naked eye.

According to this invention, photo-product intermediates and photo-product compositions can be made by effecting contact of the reactants in a solvent. It is necessary only that the reaction medium be such that each of the reactants are soluble in it. Water alone can be utilized, but does not impart sufficient solubility to yield optimum results. Other suitable solvents are alcohols, with preferred solvents including lower alkanols, such as ethanol, isopropanol, n-propanol, isobutanol, n-butanol, and the like. Aqueous alcohol solvents and various mixtures of these solvents can also be utilized.

An oxygen source within the scope of this invention is molecular oxygen. Air contains sufficient oxygen to meet the objectives of this invention. It has been observed that bubbling pure molecular oxygen through the reaction formula speeds up the reaction rate. Other oxygen sources providing molecular oxygen may also be employed. The photo-product will not, however, form in the absence of oxygen. For example, Reaction Product IV reactants under a nitrogen or argon atmosphere in the absence of oxygen, did not produce a photo-product composition of the present invention.

Figure 2:
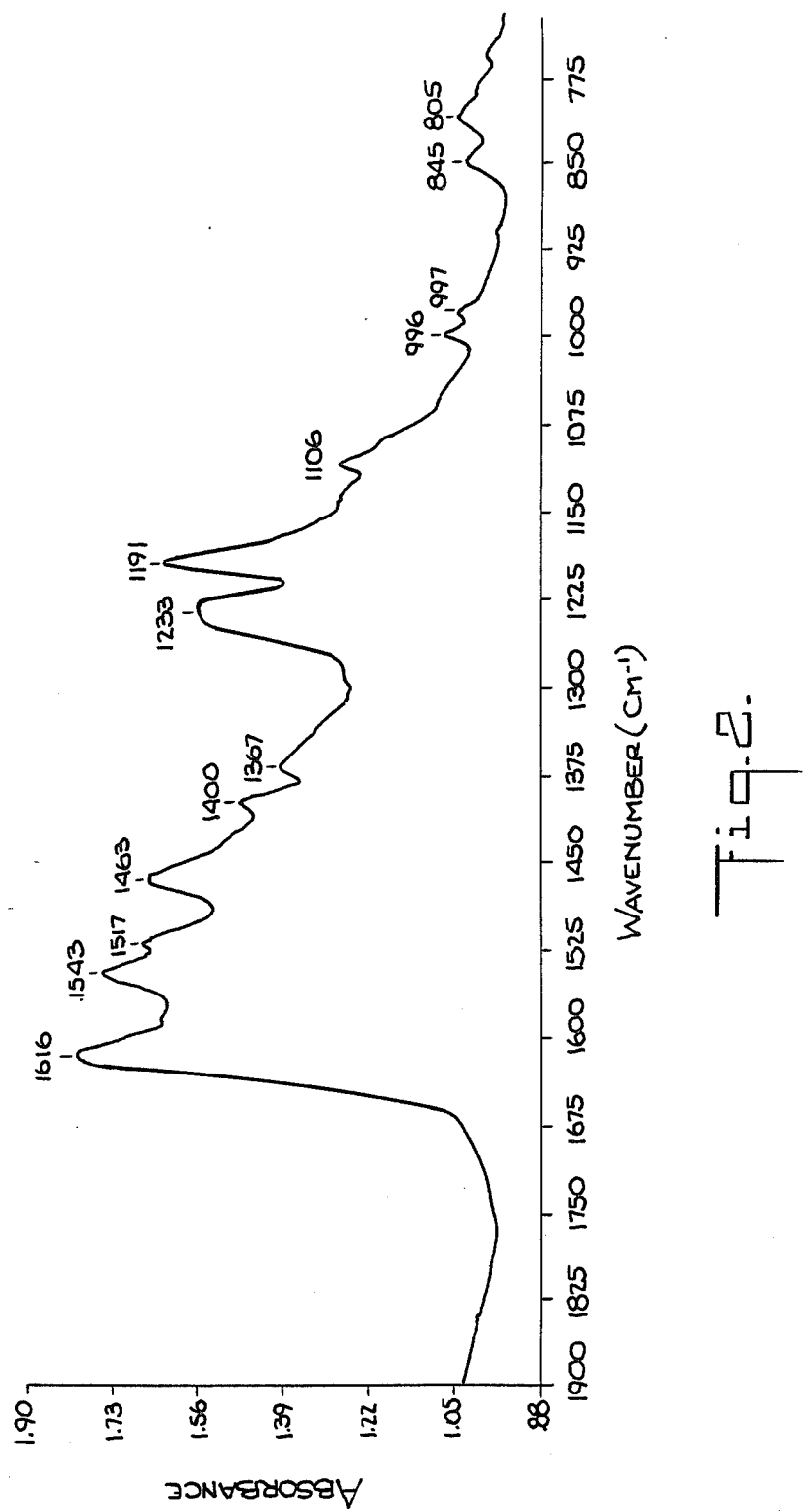
FIG. 2 is the infrared absorption spectrum for a Reaction Product I composition of the same Intermediate Reaction Product I composition as shown in FIG. 1, but after exposure to fluorescent light for 5 days, as discussed herein.

FIG. 1 shows the infrared absorption spectrum of one particular Intermediate Reaction Product I composition before exposure to light. FIG. 2 shows the corresponding Reaction Product I photo-product composition after exposure to fluorescent light in the presence of air for 5 days. The reactant mixture contains 1% ammonium hydroxide, 4% THBP and 95% ethanol. Trace amounts of zinc were detected in this photo-product by x-ray analysis. The absorption spectrum of FIG. 1 was determined by dipping a silver chloride plate in the above solution, air drying the sample and placing it into an FTIR instrument (a Nicolet model 60SX Fourier Transform Infrared Spectrometer) prior to exposure to light. The infrared absorption spectrum of FIG. 2 was determined by the same procedure except that, the silver chloride plate was left in the Reaction Product I formula and exposed to fluorescent light in a laboratory for 5 days in a normal atmospheric environment. After 5 days, the plate was removed, washed with ethanol, then washed with acetone, dried and placed into the FTIR.

In another embodiment, this invention consists of a process of making a photo-product intermediate composition suitable for providing a photo-product upon exposure to light in the presence of an oxygen source comprising contacting: (a) 2,2′,4,4′-tetrahydroxybenzophenone; (b) ammonium hydroxide; and (c) at least one metal salt; in a solvent. This invention also relates to a process for making a photo-product which is formed by exposing the above reactant mixture to light in the presence of an oxygen source. Additionally, the photo-product intermediates and the photo-product compositions ("Reaction Product II") made by the above-noted process are within the scope of this invention.

The metal salts that can be utilized in accordance with this aspect of the invention include the metal cations zinc, cadmium, copper, silver, nickel, zirconium, palladium, platinum, cobalt, rhodium, iron, ruthenium, manganese, tin, lead, polonium, mercury, and the like, and mixtures thereof, in combination with various inorganic and organic anions, such as sulfate, nitrate, bromide, chloride, acetate, formate, benzosulfonate, benzoate, and carbonate, and the like, and mixtures thereof. The preferred metal salts include nickel chloride, cobalt chloride, silver acetate, zinc acetate and copper acetate.

The concentrations of the three reactants used to form Reaction Product II are as follows: THBP from about 0.01% to 10%, ammonium hydroxide from about 0.01 to 10%, and metal salt from about 0.001 to 5%. All weight percents are bssed on the weight of the total composition.

A preferred product is formed from a ratio of at least about 18 moles of THBP, 5 moles of ammonium hydroxide, and 1 mole of a metal salt, such as nickel chloride. The maximum concentration of reactants in the process, especially THBP, is limited by solubility.

The reaction conditions described above for Reaction Proces and Product I apply to the process to form Reaction Product II, except that the photo-product reaction proceeds at a faster rate. A noticeable film (a blue-green metallic film) is usually observed within 24 hours upon exposure to sunlight in the presence of oxygen. It is postulated that the addition of the metal salt permits the formation of an intermediate metal-ligand-coordination complex which improves both the energy barrier properties of Reaction Product II and the rate of reaction.

The rate of reaction is, as previously explained, dependent on the type and intensity of light. However, the rate of reactivity is, in general, also dependent on the metal cation utilized, with the general order of reactivity from the most active to the least active as follows: manganese ($Mn^{+2}$), ruthenium ($Ru^{+2}$), iron ($Fe^{+2}$), rhodium ($Rh^{+2}$), cobalt ($Co^{+2}$), platinum ($Pt^{+2}$), palladium ($Pd^{+2}$), copper ($Cu^{+2}$), lead ($Pb^{+2}$), nickel ($Ni^{+2}$), cadmium ($Cd^{+2}$), and zinc ($Zn^{+2}$).

The Reaction Product II photo-product when using nickel chloride as the metal salt is evidenced by the formation of a blue-green metallic film which forms on the substrate that is in contact with the reactants. For example, if the reactants are mixed in a glass vial, the photo-product will form and tenaciously adhere to the glass substrate upon exposure to light in the presence of oxygen.

This invention, in another aspect, consists of a process for making a photo-product intermediate composition suitable for providing a photo-product upon exposure to light in the presence of an oxygen source comprising contacting: (a) 2,2′,4,4′-tetrahydroxybenzophenone; (b) at least one metal salt; and (c) at least one amine; in a solvent. This invention also relates to a process for making photo-product which is formed by exposing the above reactant mixture to light in the presence of oxygen. Additionally, the photo-product intermediates and photo-product compositions ("Reaction Product III") made by the above process are within the scope of this invention.

The amines that are used in accordance with this invention include triethanolamine, monomethanolamine, diethanolamine, butylamine, n-amylamine, and the like. It is believed that the amine, in particular the preferred amine, triethanolamine, assists in the deprotonation of THBP prior to the photo-reaction. The amines mentioned above, including others, also have the capacity to form an amine-metal coordination complex, which is believed to complex with the deprotonated THBP during the process. Additionally, the amine-metal complex hinders the formation of insoluble metal hydroxides.

The Reaction Product III formula can be conveniently utilized in commercial use. However, to inhibit the photo-reaction from occurring prior to application by the user, a stabilized formulation has been developed. In the stabilized formulation, acetic acid or carbonic acid is added to the reactants of Reaction Product III. The pH of this formulation is typically about 6.2±0.2.

Upon application, most of the acetic acid volatilizes or, if used, the carbonic acid converts to carbon dioxide and water. This raises the pH thereby allowing the THBP to be slowly deprotonated by the triethanolamine and complexed with the metal-amine. It is believed that the acetic acid or carbonic acid initially stabilizes the THBP and prevents the deprotonation reaction from occurring.

This stabilized photo-product film initially becomes visible in about 24 hours upon exposure to sunlight in the presence of oxygen and continues reacting for one to two weeks thereafter, producing a fully-developed film within that time period.

The concentration ranges of the three reactants employed in the Reaction Product III mix, in accordance with this invention, are as follows: about 0.01 to 10% of THBP, about 0.001 to 5% of at least one metal salt, preferably copper acetate, and about 0.01 to 2% of at least one amine, preferably triethanolamine. The amount of acetic acid or carbonic acid required to prevent deprotonization of THBP is usually the amount required to lower the pH of the reactant mixture to about 6 or below. Examples of these formulations are given in Table 2 hereafter.

Figure 3:
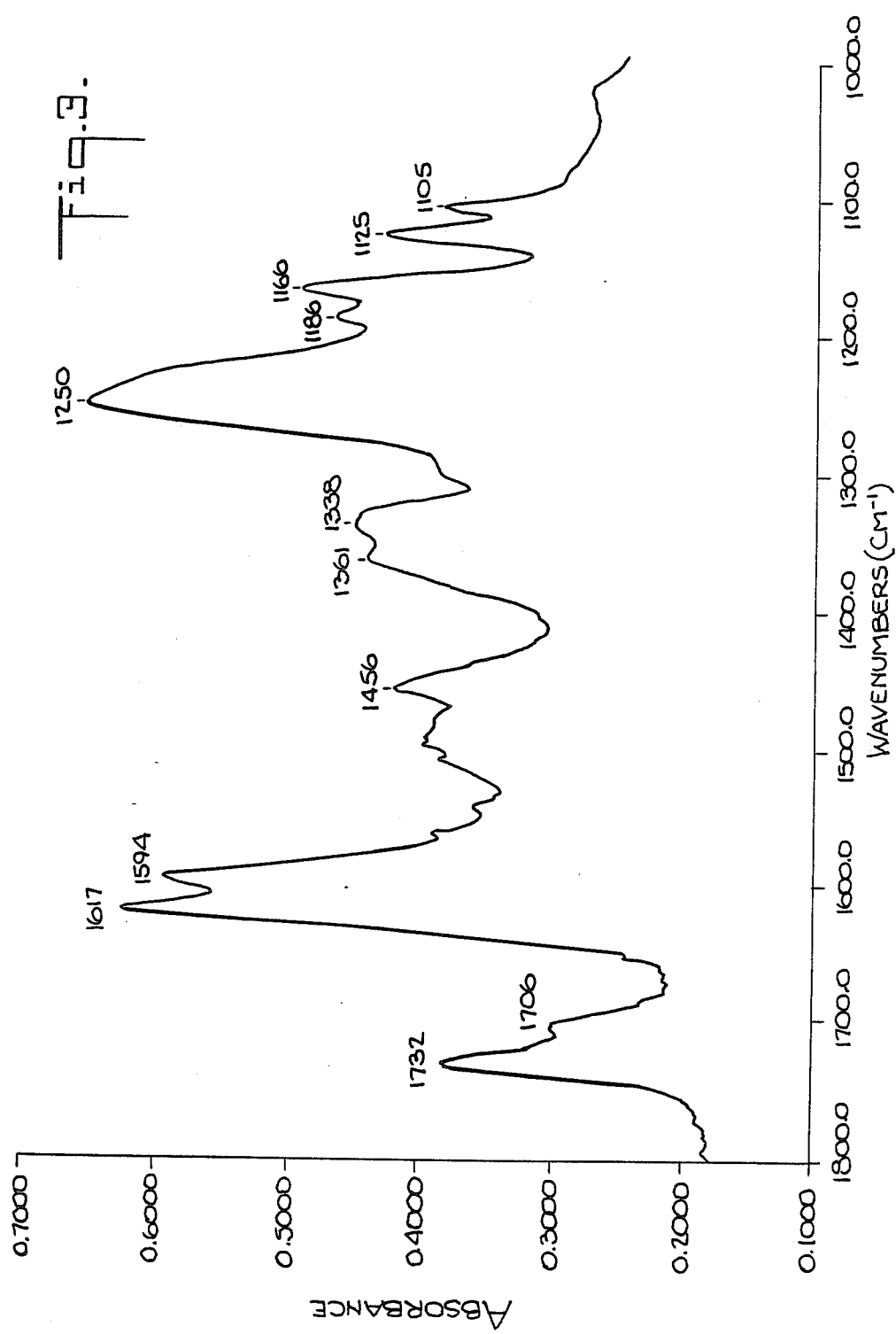
FIG. 3 is the infrared absorption spectrum for an Intermediate Reaction Product IV composition, prior to light exposure, as described herein.
Figure 4:
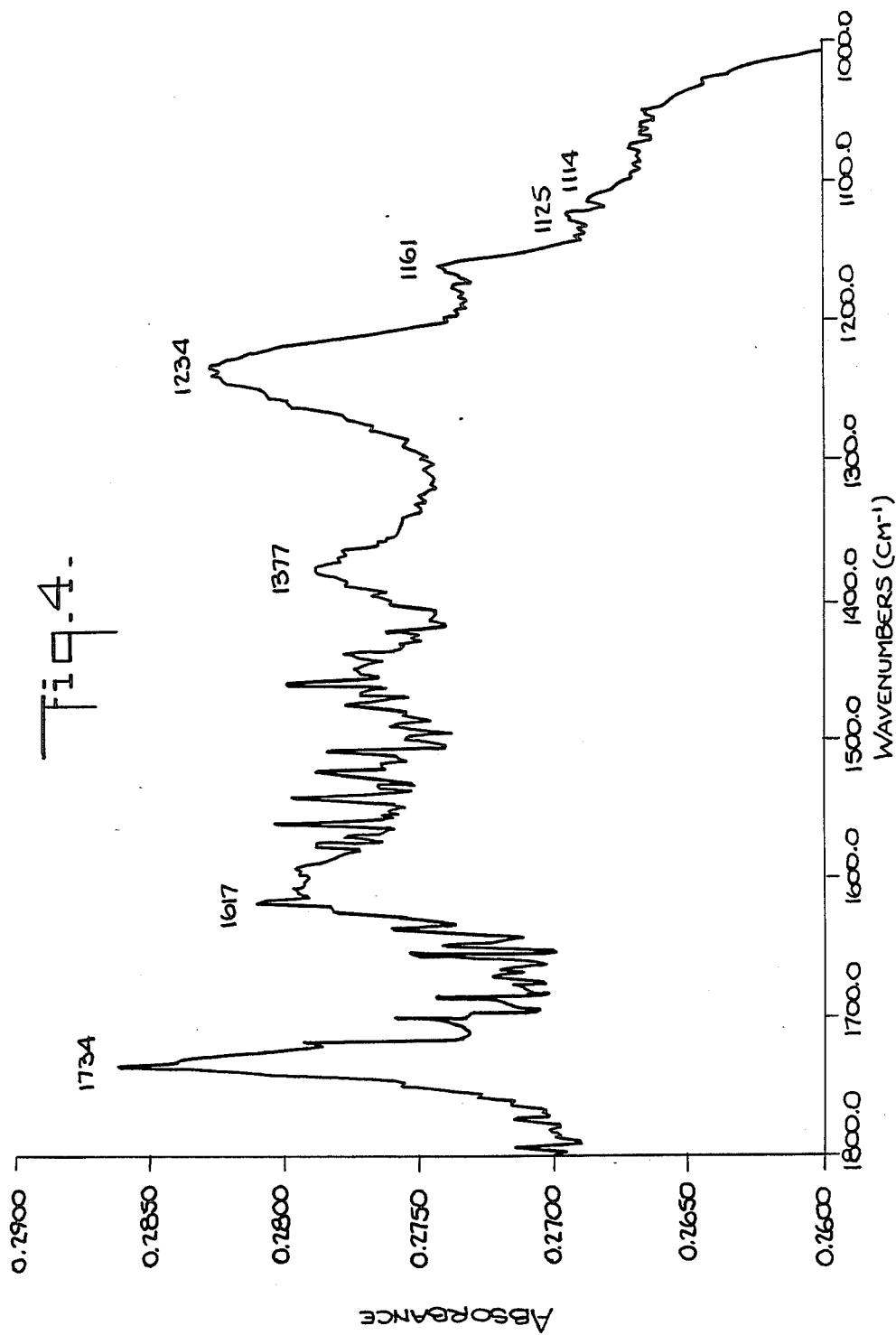
FIG. 4 is the infrared absorption spectrum for a Reaction Product IV composition of the same Intermediate Reaction Product IV composition as shown in FIG. 3, but after exposure to fluorescent light for 4 days, as disclosed herein.

FIG. 3 shows the infrared absorption spectrum of one particular Intermediate Reaction Product III composition before exposure to light. FIG. 4 shows the corresponding Reaction Product III photo-product composition after exposure to a mercury arc vapor lamp in the presence of air for approximately 9 hours. The reactant mixture contains 4.000% THBP, 76.75% ethanol, 4.00% deionized water, 8.00% alcohol, 1.00% triethanolamine, 0.5% acetic acid (99.9% concentration), 0.75% copper acetate, and 5.00% of a polymer consisting of 60% ethyl acrylate and 40% methylmethacrylate. The absorption spectrum of FIG. 3 was determined by dipping a silver chloride plate in the above solution, air drying the sample and placing it into an FTIR instrument prior to exposure to light. The infrared absorption spectrum of FIG. 4 was determined by the same procedure except that, the silver chloride plate was left in the Reaction Product III formula and exposed to the mercury arc vapor lamp for approximately 9 hours in a normal atmosphere. After exposure, the plate was removed, washed with ethanol, then washed with acetone, dried and placed into the FTIR.

The most preferred embodiment of this invention consists of a process for making a photo-product intermediate composition suitable for providing a photo-product upon exposure to light in the presence of an oxygen source comprising contacting: (a) 2,2',4,4'-tetrahydroxybenzophenone; (b) ammonium hydroxide; (c) at least one metal salt; and (d) at least one amine; in a solvent. The invention also relates to a process for making the photo-product, which is formed by exposing the above reactant mixture to light in the presence of an oxygen source. Additionally, the photo-product intermediate and photo-product composition ("Reaction Product IV") made by the above process are within the scope of this invention.

The only benzophenone found that meets the objectives of this invention and provides a suitable photo-product is 2,2',4,4'-tetrahydroxybenzophenone. Additionally, sources of ammonium and hydroxyl ion, other than ammonium hydroxide, have not proven effective in producing a photo-product of this invention in Reaction Product IV formulas.

Figure 8:
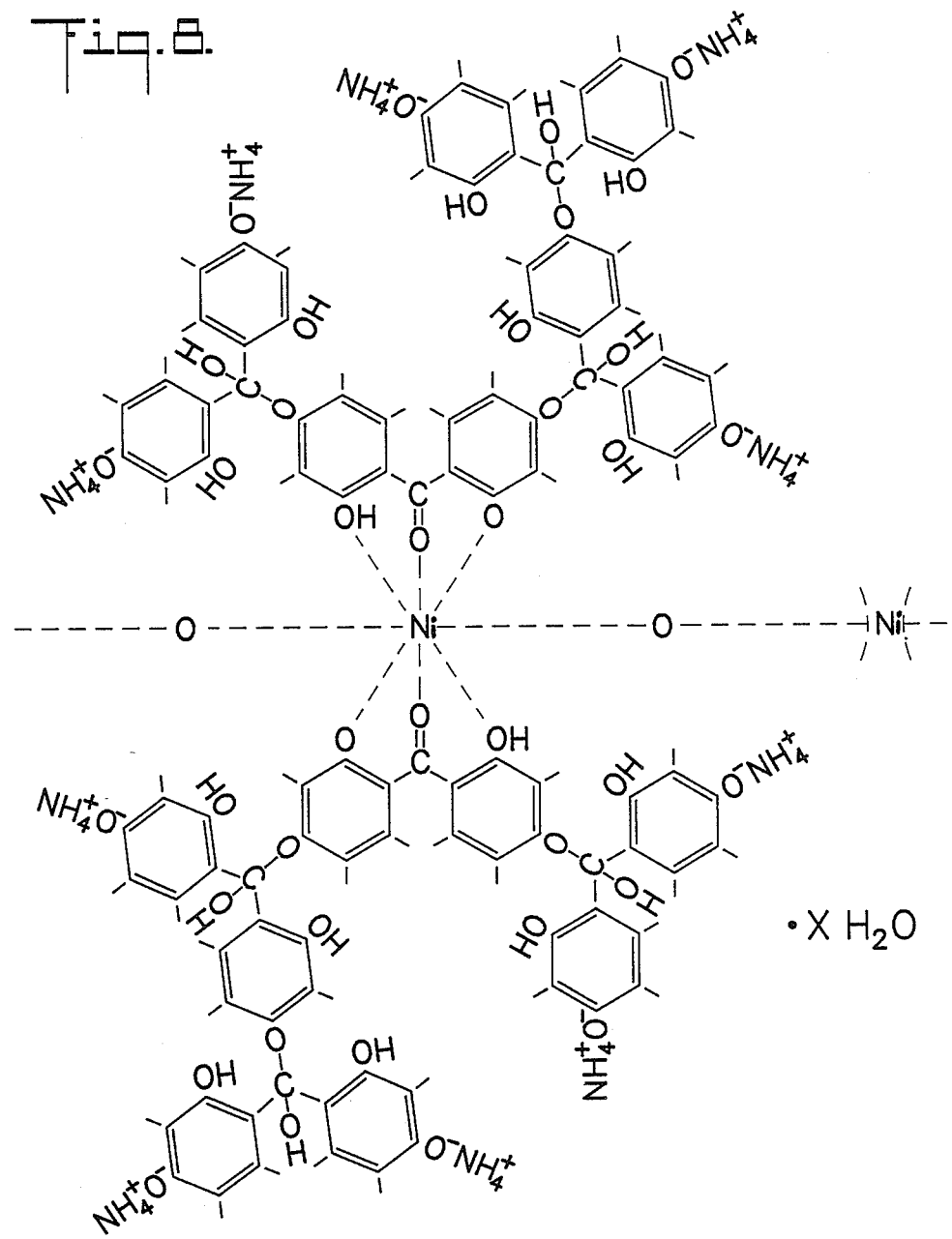
FIG. 8 is a theoretical structure of a Reaction Product IV composition.

The formulas of the reaction products of this invention are unknown. It is postulated that, in the first step of the process, the ammonium hydroxide deprotonates the hydroxyl group adjacent to the THBP carbonyl group. Under the influence of light and oxygen, the deprotonated THBP may form a diradical and then form both a coordination complex with the metal cation and an addition product with another THBP molecule having a possible formula as shown in FIG. 8.

Typical concentrations in the Reaction Product IV formulations are given in Table 1 below:

TABLE 1

Reaction Product IV Formulations

| Ingredients | General | Preferred | Most Preferred |
|---|---|---|---|
| THBP | 0.01 to 10% | 3.0 to 5.0% | 4.0% |
| NH$_4$OH | | | |
| (28.5% conc.) | 0.1 to 10% | 0.25 to 1.75% | 1.0% |
| (100% conc.) | 0.1 to 1% | 0.1 to 0.5% | 0.3% |
| Metal salt | 0.001 to 5% | 0.05 to 0.5% | 0.2% |
| Amine | 0.001 to 2% | 0.25 to 1% | 0.6% |
| H$_2$O | 0 to 15% | 6 to 10% | 8.0% |
| Alcohol | balance to 100% | balance to 100% | balance to 100% |

The production of Reaction Product IV from the reaction formulation is typically carried out as described above for Reaction Products I and II. When this formulation is contacted with a substrate, such as glass, and exposed to sunlight in the presence of oxygen, a visible photo-film (blue-green metallic sheen) is produced in a few hours, especially with the faster reacting metals, such as copper, manganese and iron. Exposure of this formulation to a mercury arc lamp in the presence of oxygen produces a visible photo-film within a few minutes.

Although applicants do not wish to be bound by any particular theory, the photo-ligand-metal-coordination complex of Reaction Product IV is believed to proceed as follows: THBP, preferably at least about 6 moles and more preferably at least about 18 moles, is mixed with at least 5 moles of ammonium hydroxide, in a suitable solvent, preferably an aqueous alcohol solvent, to form deprotonated THBP. The metal salt, preferably about 1 mole of a nickel salt is then mixed with 5 moles of an amine, preferably triethanolamine, to form a nickel salt-triethanolamine coordination complex. This complex is then mixed with the deprotonated THBP to form a metal-coordination complex that upon exposure to light in the presence of oxygen forms a photo-product of the present invention.

The photo-products of this invention are insoluble in the reaction media and many other solvents, and therefore, are long lasting and durable. Once applied, the photo-product cannot be removed without chemical treatment. To date, only strong solvents, such as dimethyl sulfoxide, appear to solubilize or form a complex with the photo-film to effect its removal. Additionally, dimethyl formamide will dissolve Reaction Product I. It is known, however, that the photo-product film will form water-soluble salts with appropriate bases. For example, the photo-film can be dissolved by a weak base, such as potassium or ammonium hydroxide, at pH above 10. Typically, the film is solubilized at a pH from 10.2 to 10.5. The photo-product can be precipitated as a solid from these basic solutions by the addition of an acid, such as acetic acid, to lower the pH to below about 7.0.

The process of forming the salt of a photo-product and precipitating it out again provides the potential for superior application properties.

The pH ranges of the photo formulas of Reaction Products I, II and IV typically range from about 8.5 to 9.9.

The addition of iodine to the reaction mixtures of this invention has been found to further reduce the transmittance of ultraviolet and infrared radiation in accordance with the teachings of this invention. The iodine is mixed with the reactants prior to exposure to light to yield these beneficial results. The concentration of iodine that may be utilized varies from about 0.001% to about 5%, with a range of 0.01% to 1% being preferred. These percentages are weight precents based on the total weight of the composition.

The reaction mixtures of this invention also preferably employ various polymers, such as ethyl acrylate and/or methylmethacrylate, or other alcohol-soluble resin polymers, that act as a matrix so that the reactants can be easily applied to substrates such as windows, and thereby allow the formation of the photo-product on the substrate.

Figure 5:
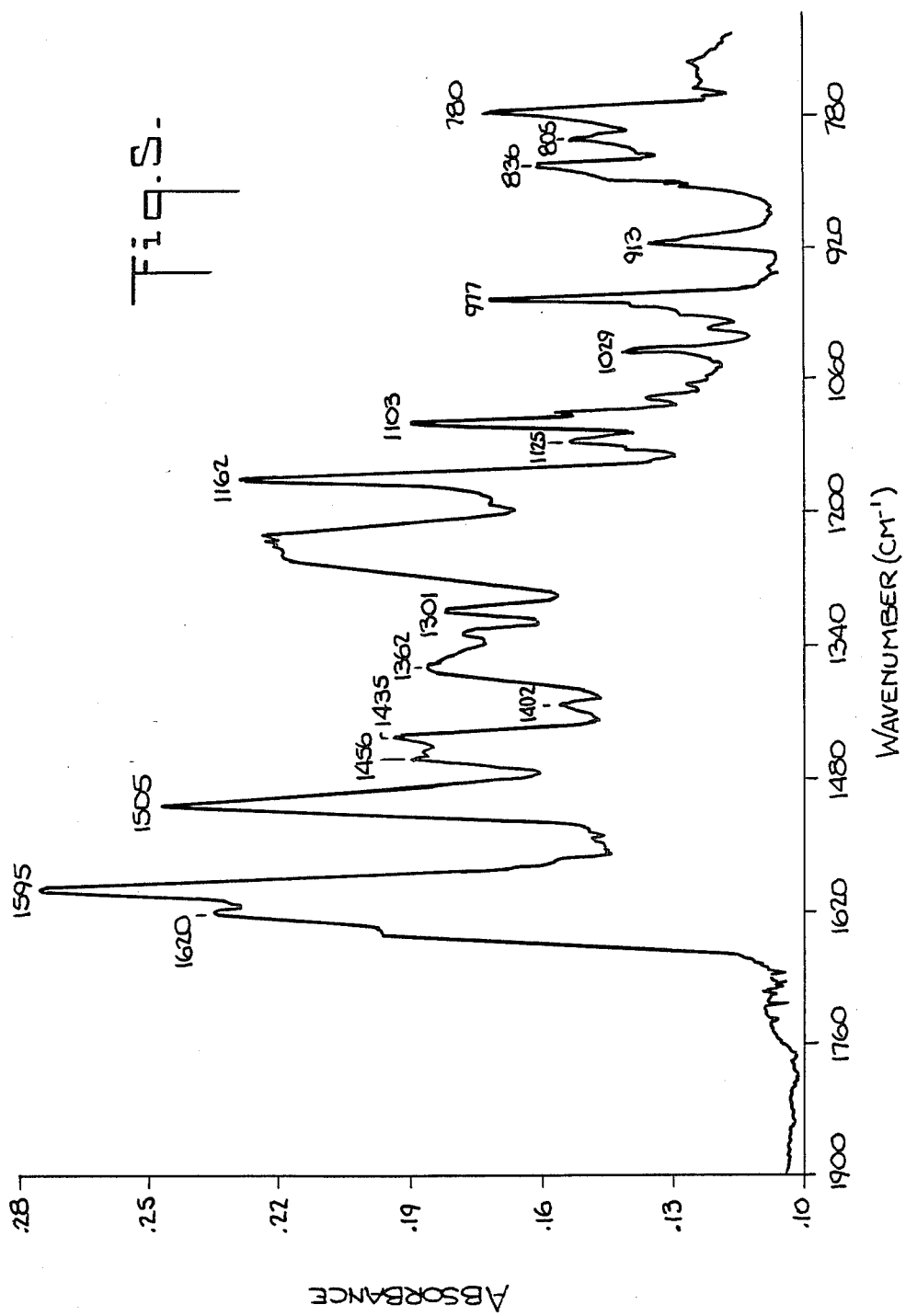
FIG. 5 is the infrared absorption spectrum for an Intermediate Reaction Product III composition, prior to light exposure, as described herein.
Figure 6:
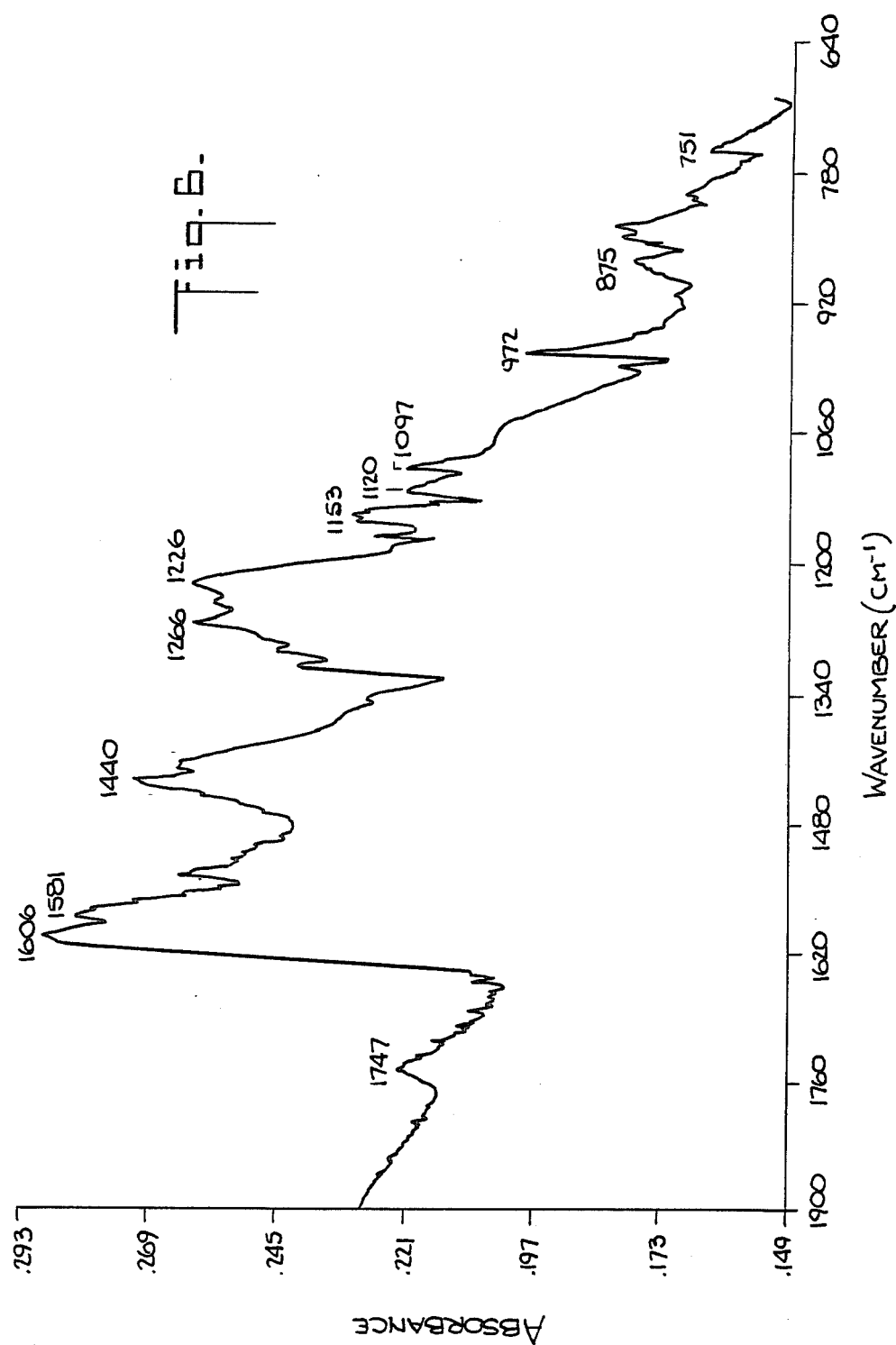
FIG. 6 is the infrared absorption spectrum for a Reaction Product III composition of the same Intermediate Reaction Product III composition as shown in FIG. 5, but after exposure to a mercury arc lamp for 9 hours, as discussed herein.

FIGS. 5 and 6 show the infrared absorption spectrum of one particular Reaction Product IV formula, containing 4.14% THBP, 86.0% ethanol, 0.63% triethanolamine, 8.00% deionized water, 1.03% ammonium hydroxide (at 28.5% concentration) and 0.2% nickel chloride, before and after exposure to fluorescent light in the presence of oxygen for four days, respectively. These absorption spectrum were determined in the same manner as described for FIGS. 1 and 2.

Figure 7:
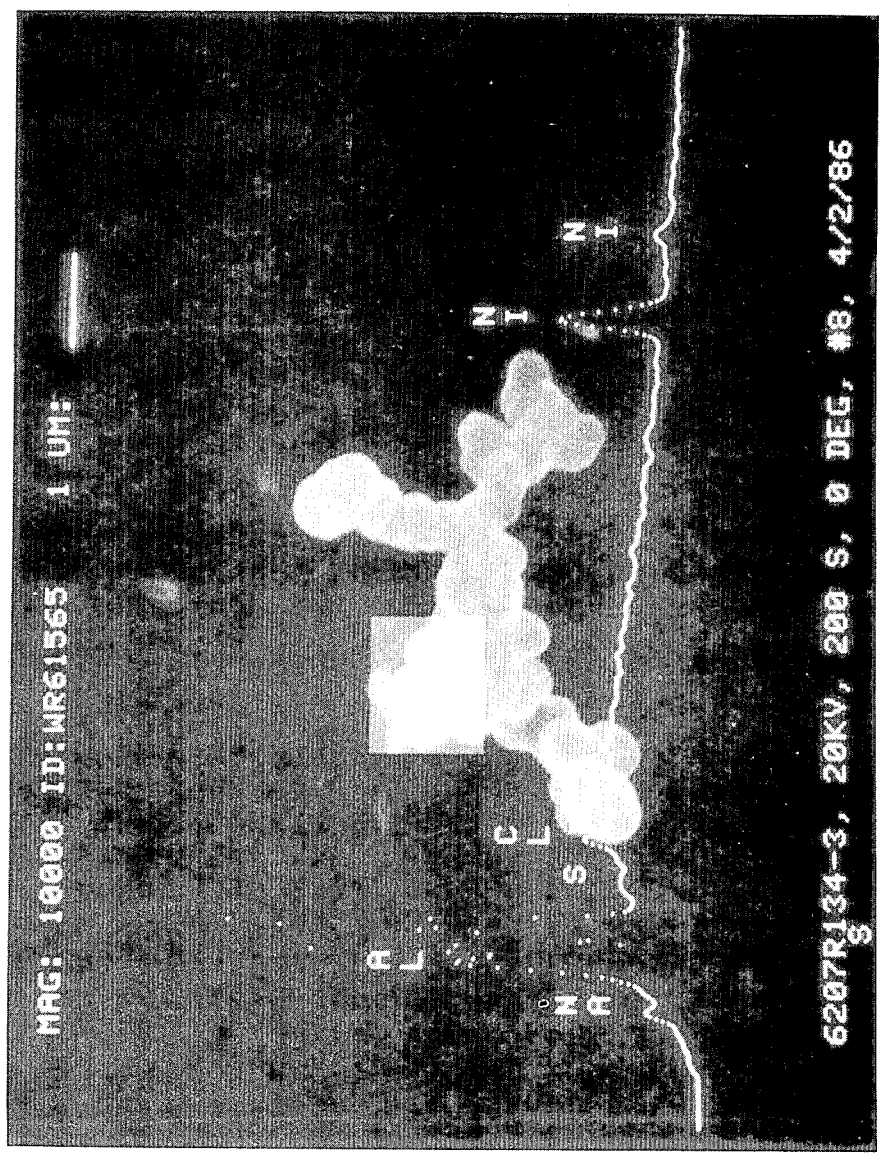
FIG. 7 is an electron photomicrograph of a preferred Reaction Product IV composition.

FIG. 7 is an electron photomicrograph of the Reaction Product IV photo-product of FIG. 4. Glass tubes coated with this photo-product were broken with a hammer and individual fragments were glued, inner surface up, onto specimen stubs and then carbon coated by evaporation. The specimens were examined in the scanning electron microscope using a 20 kV beam at a magnification of 10,000×, with no specimen tilt.

Other aspects and embodiments of this invention are shown in the following Examples which are illustrative of scope.

EXAMPLES 1–15

Examples 1–15 of Table 2 were prepared by contacting the ingredients shown in Table 2 and exposing them to light, either sunlight or artificially produced light, on window glass to provide photo-product films exhibiting reductions in both ultraviolet and infrared transmittance. These films typically vary in thickness from about 1000 to 3000 angstroms.

TABLE 2

| | Reaction Product III Formulations | | | | | | | | | | | | | | |
|---|---|---|---|---|---|---|---|---|---|---|---|---|---|---|---|
| EXAMPLES | 1 | 2 | 3 | 4 | 5 | 6 | 7 | 8 | 9 | 10 | 11 | 12 | 13 | 14 | 15 |
| Ethanol | 86.7 | 87.3 | 77.2 | 86.3 | 86.1 | 86.39 | 85.6 | 85.0 | 84.96 | 84.5 | 80.5 | 80.5 | 78.5 | 81.75 | 76.9 |
| Deionized Water | 8.0 | 8.0 | 8.0 | 8.0 | 8.0 | 8.2 | 8.1 | 8.0 | 7.99 | 8.0 | 8.0 | — | — | — | 4.0 |
| THBP | 4.0 | 4.0 | 4.0 | 4.0 | 4.0 | 3.94 | 4.0 | 4.5 | 4.59 | 4.5 | 4.0 | 2.0 | 3.5 | 4.0 | 4.0 |
| TEA | 0.5 | 0.6 | 0.6 | 1.0 | 1.0 | 1.1 | 1.07 | 1.0 | 1.1 | 1.0 | 1.0 | 1.0 | 1.0 | 1.0 | 1.0 |
| Metal Salt | 0.4[1] | 0.2[2] | 0.2[2] | 0.2[3] | 0.2[3] | 0.5[3] | 1.0[3] | 1.0[3] | 0.99[4] | 1.0[3] | 1.0[3] | 1.0[3] | 1.5[3] | 0.75[3] | 1.0[3] |
| Acetic Acid[a] | 0.4 | 0.1 | 10.0 | 0.5 | 0.5 | 0.54 | 0.54 | 0.5 | 0.65 | 0.5 | 0.5 | 0.5 | 0.5 | 0.5 | 1.0[g] |
| Stearyl[d] or benzyl[e] alcohol | — | — | — | — | 0.2[d] | — | — | — | — | — | 8.0[e] | 10.0[e] | 10.0[e] | 8.0[e] | 8.0 |
| Matrix Polymer | — | — | — | — | — | — | — | — | — | 0.5[b] | 5.0[c] | 5.0[c] | 5.0[c] | 4.0[c] | 5.0[c] |

[1]silver acetate
[2]FeCl$_2$.4H$_2$O
[3]copper acetate
[4]zinc acetate
[a]99.9% concentrated acetic acid
[b]Carbsoset 525 B. F. Goodrich
[c]60% ethyl acrylate and 40% methylmethacrylate
[g]CO$_2$ gas

EXAMPLES 16–25

The Reaction Product IV formulas of Table 3 were also prepared by contacting the ingredients shown and exposing them to light, either sunlight or artificially produced light, on window glass to provide photo-product films which significantly reduced the transmission of infrared and ultraviolet radiation.

TABLE 3

| | Reaction Product IV Formulations | | | | | | | | | |
|---|---|---|---|---|---|---|---|---|---|---|
| EXAMPLES | 16 | 17 | 18 | 19 | 20 | 21 | 22 | 23 | 24 | 25 |
| Ethanol | 86.0 | 87.4 | 90.85 | 86.0 | 86.0[a] | 86.1 | 95.4 | 86.1 | 86.2 | 86.2 |
| THBP | 4.0 | 2.0 | 3.0 | 4.14 | 4.14 | 4.0 | 2.0 | 4.0 | 4.0 | 4.0 |
| TEA | 0.5 | 0.5 | 0.75 | 0.63 | 0.63 | 0.5 | 0.5 | 0.5 | 0.6 | 0.6 |
| NH$_4$OH (28.5%) | 1.0 | 1.0 | 5.0 | 1.03 | 1.03 | 1.0 | 1.0 | 1.0 | 1.0 | 1.0 |
| Deionized Water | 8.0 | 8.0 | — | 8.0 | 8.0 | 8.0 | — | 8.0 | 8.0 | 8.0 |
| Metal Salt | 0.5[1] | 0.1[1] | 0.4[1] | 0.2[1] | 0.2[1] | 0.4[2] | 0.1[3] | 0.4[4] | 0.2[5] | 0.2[6][7] |
| Benzyl Alcohol | 1.0 | — | — | — | — | — | 1.0 | — | — | — |

[1]NiCl$_2$.H$_2$O
[2]silver acetate
[3]iron chloride (FeCl$_2$.H$_2$O)
[4]copper acetate monohydrate
[5]MnCl$_2$.4H$_2$O
[6]ZnCl$_2$
[7]CuCl$_2$.H$_2$O
[a]isopropanol

EXAMPLE 26

A Reaction Product IV composition was prepared by contacting 4.14% THBP, 0.63% triethanalamine, 1.03% ammonium hydroxide (28.5% conc.), 0.2% of $NiCl_2.6H_2O$, 8.0% deionized water, and 86.0% ethanol, then exposing this mixture to light in the presence of oxygen. Glass vials coated with the photo-product were then rinsed with 100 ml of distilled water containing 4 grams of 28.5% sodium hydroxide in order to remove the photo-compound from the sides of the container. A salt solution of this photo-compound was then precipitated with acetic acid, centrifuged and washed with distilled water and absolute alcohol and dried. The elemental analysis showed 47.71% carbon, 3.72% hydrogen, 5.54% nitrogen, 2.3% nickel and 12.23% residue.

EXAMPLE 27

A typical Reaction IV composition product containing iodine was prepared by contacting 4.0% THBP, 86.1% ethanol, 0.1% iodine (99.9% concentration), 0.6% triethanolamine, 8.0% deionized water, 1.0% ammonium hydroxide (28.5% concentration), and 0.2% copper acetate, or nickel chloride; and then exposing this mixture to light in the presence of oxygen.

What is claimed is:

1. A process for making a photo-product intermediate composition having a pH from about 7 to 10.5 suitable for providing a photo-product upon exposure to light in the presence of an oxygen source comprising contacting:
   (a) 2,2',4,4'-tetrahydroxybenzophenone;
   (b) ammonium hydroxide; and
   (c) optionally a trace amount of at least one metal selected from the group consisting of zinc, copper, nickel, silver, iron, manganese, lead, cobalt, zirconium, mercury, palladium, cadmium, ruthenium, rhodium, and mixtures thereof;
   in a solvent.

2. The process of claim 1 wherein the solvent is selected from the group consisting of ethanol, isopropanol, n-propanol, isobutanol, n-butanol, mixtures and aqueous mixtures thereof.

3. A process for making a photo-product comprising:
   (1) contacting:
   (a) 2,2',4,4'-tetrahydroxybenzophenone;
   (b) ammonium hydroxide; and
   (c) optionally a trace amount of at least one metal selected from the group consisting of zinc, copper, nickel, silver, iron, manganese, lead, cobalt, zirconium, mercury, palladium, cadmium, ruthenium, rhodium, and mixtures thereof; in a solvent to form a reactant mixture having a pH from about 7 to 10.5; and
   (2) exposing the reactant mixture to light in the presence of an oxygen source.

4. The process of claim 3 wherein a photo-product is formed upon exposure to light in the wavelength range of about 340 to 360 nanometers.

5. A process for making a photo-product intermediate composition having a pH from about 7 to 10.5 suitable for providing a photo-product upon exposure to light in the presence of an oxygen source comprising contacting:
   (a) 2,2',4,4'-tetrahydroxybenzophenone;
   (b) ammonium hydroxide; and
   (c) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof;
   in a solvent.

6. The process of claim 5 wherein the solvent is selected from the group consisting of ethanol, isopropanol, n-propanol, isobutanol, n-butanol, mixtures and aqueous mixtures thereof.

7. A process for making a photo-product comprising:
   (1) contacting:
   (a) 2,2',4,4'-tetrahydroxybenzophenone;
   (b) ammonium hydroxide; and
   (c) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof;
   in a solvent to form a reactant mixture having a pH from about 7 to 10.5; and
   (2) exposing the reactant mixture to light in the presence of an oxygen source.

8. The process of claim 7 wheren the anion of the metal salt is selected from the group consisting of sulfate, nitrate, bromide, chloride, acetate, formate, carbonate, benzenesulfonate, benzoate and mixtures thereof.

9. The process of claim 7 wherein the alcohol is selected from the group consisting of ethanol, isopropanol, n-propanol, isobutanol, n-butanol, mixtures and aqueous mixtures thereof.

10. A process for making a photo-product intermediate composition having a pH from about 7 to 10.5 suitable for providing a photo-product upon exposure to light in the presence of an oxygen source comprising contacting:
    (a) 2,2',4,4'-tetrahydroxybenzophenone;
    (b) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof; and
    (c) at least one amine;
    in a solvent.

11. The process of claim 10 wherein the anion of the metal salt is selected from the group consisting of sulfate, nitrate, bromide, chloride, acetate, formate, carbonate, benzenesulfonate, benzoate and mixtures thereof.

12. The process of claim 10 wherein the metal salt is selected from the group consisting of nickel chloride, cobalt chloride, silver acetate, copper acetate and mixtures thereof.

13. The process of claim 10 wherein the alcohol is selected from the group consisting of ethanol, isopropanol, n-propanol, isobutanol, n-butanol, mixtures and aqueous mixtures thereof.

14. The process of claim 10 wherein the amine is selected from the group consisting of triethanolamine, diethanolamine, ethanolamine, monomethanolamine, butylamine, n-amylamine and mixtures thereof.

15. A process for making a photo-product comprising:
    (1) contacting:
    (a) 2,2',4,4'-tetrahydroxybenzophenone;
    (b) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof; and
  (c) at least one amine;
in a solvent to form a reactant mixture having a pH from about 7 to 10.5; and
  (2) exposing the reactant mixture to light in the presence of an oxygen source.

16. The process of claim 15 wherein the anion of the metal salt is selected from the group consisting of sulfate, nitrate, bromide, chloride, acetate, formate, carbonate, benzenesulfonate, benzoate and mixtures thereof.

17. The process of claim 15 wherein the metal salt is selected from the group consisting of nickel chloride, cobalt chloride, silver acetate, copper acetate and mixtures thereof.

18. The process of claim 15 wherein the alcohol is selected from the group consisting of ethanol, isopropanol, n-propanol, isobutanol, n-butanol, mixtures and aqueous mixtures thereof.

19. The process of claim 15 wherein the amine is selected from the group consisting of triethanolamine, diethanolamine, ethanolamine, monomethanolamine, butylamine, n-amylamine and mixtures thereof.

20. A process for making a photo-product intermediate composition having a pH from about 7 to 10.5 suitable for providing a photo-product upon exposure to light in the presence of an oxygen source comprising contacting:
  (a) 2,2′,4,4′-tetrahydroxybenzophenone;
  (b) ammonium hydroxide;
  (c) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof; and
  (d) at least one amine;
in a solvent.

21. The process of claim 20 wherein the anion of the metal salt is selected from the group consisting of sulfate, nitrate, bromide, chloride, acetate, formate, carbonate, benzenesulfonate, benzoate and mixtures thereof.

22. The process of claim 20 wherein the metal salt is selected from the group consisting of nickel chloride, cobalt chloride, silver acetate, copper acetate and mixtures thereof.

23. The process of claim 20 wherein the alcohol is selected from the group consisting of ethanol, isopropanol, n-propanol, isobutanol, n-butanol, mixtures and aqueous mixtures thereof.

24. The process of claim 20 wherein the amine is selected from the group consisting of triethanolamine, diethanolamine, ethanolamine, monoethanolamine, butylamine, n-amylamine and mixtures thereof.

25. The process of claim 20 wherein the amine is triethanolamine and the metal salt is nickel chloride.

26. A process for making a photo-product comprising
(1) contacting:
  (a) 2,2′4,4′-tetrahydroxybenzophenone;
  (b) ammonium hydroxide;
  (c) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof; and
  (d) at least one amine;
in a solvent to form a reactant mixture having a pH from about 7 to 10.5, and
  (2) exposing the reactant mixture to light in the presence of an oxygen source.

27. The process of claim 26 wherein the anion of the metal salt is selected from the group consisting of sulfate, nitrate, bromide, chloride, acetate, formate, carbonate, benzenesulfonate, benzoate and mixtures thereof.

28. The process of claim 26 wherein the metal salt is selected from the group consisting of nickel chloride, cobalt chloride, silver acetate, copper acetate and mixtures thereof.

29. The process of claim 26 wherein the alcohol is selected from the group consisting of ethanol, isopropanol, n-propanol, isobutanol, n-butanol, mixtures and aqueous mixtures thereof.

30. The process of claim 26 wherein the amine is selected from the group consisting of triethanolamine, diethanolamine, ethanolamine, monomethanolamine, butylamine, n-amylamine and mixtures thereof.

31. The process of claim 26 wherein the amine is triethanolamine and the metal salt is nickel chloride.

32. A photo-product intermediate composition having a pH from about 7 to 10.5 suitable for providing a photo-product upon exposure to light in the present of an oxygen source comprising:
  (a) 2,2′,4,4′-tetrahydroxybenzophenone;
  (b) ammonium hydroxide; and
  (c) optionally a trace amount of at least one metal selected from the group consisting of zinc, copper, nickel, silver, iron, manganese, lead, cobalt, zirconium, mercury, palladium, cadmium, ruthenium, rhodium, and mixtures thereof;
in a solvent.

33. The intermediate composition of claim 32 wherein the solvent is selected from the group consisting of ethanol, isopropanol, n-propanol, isobutanol, n-butanol, mixtures and aqueous mixtures thereof.

34. A photo-product formed by exposing to light in the presence of an oxygen source, a reactant mixture having a pH from about 7 to 10.5 comprising:
  (a) 2,2′,4,4′-tetrahydroxybenzophenone;
  (b) ammonium hydroxide; and
  (c) optionally a trace amount of at least one metal selected from the group consisting of zinc, copper, nickel, silver, iron, manganese, lead, cobalt, zirconium, mercury, palladium, cadmium, ruthenium, rhodium, and mixtures thereof;
in a solvent.

35. The photo-product of claim 34 wherein the photo-product is formed upon exposure to light in the wavelength range of about 340 to 360 nanometers.

36. A photo-product intermediate composition having a pH from about 7 to 10.5 suitable for providing a photo-product upon exposure to light in the presence of an oxygen source comprising:
  (a) 2,2′,4,4′-tetrahydroxybenzophenone;
  (b) ammonium hydroxide; and
  (c) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof;
in a solvent.

37. The intermediate composition of claim 36 wherein the anion of the metal salt is selected from the group consisting of sulfate, nitrate bromide, chloride, acetate, formate, carbonate, benzenesulfonate, benzoate and mixtures thereof.

38. The intermediate composition of claim 36 wherein the alcohol is selected from the gorup consisting of ethanol, isopropanol, n-propanol, isobutanol, n-butanol, mixtures and aqueous mixtures thereof.

39. A photo-product formed by exposing to light in the presence of an oxygen source, a reactant mixture having a pH from about 7 to 10.5 comprising:
 (a) 2,2'4,4'-tetrahydroxybenzophenone;
 (b) ammonium hydroxide; and
 (c) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof;
in a solvent.

40. The composition of claim 39 wherein the anion of the metal salt is selected from the group consisting of sulfate, nitrate, bromide, chloride, acetate, formate, carbonate, benzenesulfonate, benzoate and mixtures thereof.

41. The composition of claim 39 wherein the alcohol is selected from the group consisting of ethanol, isopropanol, n-propanol, isobutanol, n-butanol, mixtures and aqueous mixtures thereof.

42. A photo-product intermediate composition having a pH from about 7 to 10.5 suitable for providing a photo-product upon exposure to light in the presence of an oxygen source comprising:
 (a) 2,2',4,4'-tetrahydroxybenzophenone;
 (b) at least one metal salt selected from the group consisting of zinc, copper, nickel, silver, iron, manganese, lead, cobalt, zirconium, mercury, palladium, cadmium, ruthenium, rhodium, and mixtures thereof; and
 (c) at least one amine;
in a solvent.

43. The intermediate composition of claim 42 wherein the anion of the metal salt is selected from the group consisting of sulfate, nitrate, bromide, chloride, acetate, formate, carbonate, benzenesulfonate, benzoate and mixtures thereof.

44. The intermediate composition of claim 42 wherein the metal salt is selected from the group consisting of nickel chloride, cobalt chloride, silver acetate, copper acetate and mixtures thereof.

45. The intermediate composition of claim 42 wherein the alcohol is selected from the group consisting of ethanol, isopropanol, n-propanol, isobutanol, n-butanol, mixtures and aqueous mixtures thereof.

46. The intermediate composition of claim 42 wherein the amine is selected from the group consisting of triethanolamine, diethanolamine, ethanolamine, monomethanolamine, butylamine, n-amylamine and mixtures thereof.

47. A photo-product formed by exposing to light in the presence of an oxygen source, a reactant mixture having a pH from about 7 to 10.5 comprising:
 (a) 2,2',4,4'-tetrahydroxybenzophenone;
 (b) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof; and
 (c) at least one amine;
in a solvent.

48. The composition of claim 47 wherein the anion of the metal salt is selected from the group consisting of sulfate, nitrate, bromide, chloride, acetate, formate, carbonate, benzenesulfonate, benzoate and mixtures thereof.

49. The composition of claim 47 wherein the metal salt is selected from the group consisting of nickel chloride, cobalt chloride, silver acetate, copper acetate and mixtures thereof.

50. The composition of claim 47 wherein the alcohol is selected from the group consisting of ethanol, isopropanol, n-propanol, isobutanol, n-butanol, mixtures and aqueous mixtures thereof.

51. The composition of claim 47 wherein the amine is selected from the group consisting of triethanolamine, diethanolamine, ethanolamine, monomethanolamine, butylamine, n-amylamine and mixtures thereof.

52. A photo-product intermediate composition having a pH from about 7 to 10.5 suitable for providing a photo-product upon exposure to light in the presence of an oxygen source comprising:
 (a) 2,2',4,4'-tetrahydroxybenzophenone;
 (b) ammonium hydroxide;
 (c) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof; and
 (d) at least one amine;
in a solvent.

53. The intermediate composition of claim 52 wherein the anion of the metal salt is selected from the group consisting of sulfate, nitrate, bromide, chloride, acetate formate, carbonate, benzenesulfonate, benzoate and mixtures thereof.

54. The intermediate composition of claim 52 wherein the metal salt is selected from the group consisting of nickel chloride, cobalt chloride, silver acetate, copper acetate and mixtures thereof.

55. The intermediate composition of claim 52 wherein the alcohol is selected from the group consisting of ethanol, isopropanol, n-propanol, isobutanol, n-butanol, mixtures and aqueous mixtures thereof.

56. The intermediate composition of claim 52 wherein the amine is selected from the group consisting of triethanolamine, diethanolamine, ethanolamine, monomethanolamine, butylamine, n-amylamine and mixtures thereof.

57. The intermediate composition of claim 52 wherein the amine is triethanolamine and the metal salt is nickel chloride.

58. A photo-product formed by exposing to light in the presence of an oxygen source, a reactant mixture having a pH from about 7 to 10.5 comprising:
 (a) 2,2',4,4'-tetrahydroxybenzophenone;
 (b) ammonium hydroxide;
 (c) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof; and
 (d) at least one amine;
in a solvent.

59. The composition of claim 58 wherein the anion of the metal salt is selected from the group consisting of sulfate, nitrate, bromide, chloride, acetate, formate, carbonate, benzenesulfonate, benzoate and mixtures thereof.

60. The composition of claim 58 wherein the metal salt is selected from the group consisting of nickel chloride, cobalt chloride, silver acetate, copper acetate and mixtures thereof.

61. The composition of claim 58 wherein the alcohol is selected from the group consisting of ethanol, isopropanol, n-propanol, isobutanol, n-butanol, mixtures and aqueous mixtures thereof.

62. The composition of claim 58 wherein the amine is selected from the group consisting of triethanolamine, diethanolamine, ethanolamine, monomethanolamine, butylamine, n-amylamine and mixtures thereof.

63. The composition of claim 58 wherein the amine is triethanolamine and the metal salt is nickel chloride.

64. A photo-product composition suitable for reducing the transmission of electromagnetic radiation in the infrared and ultraviolet range, containing the elements carbon, hydrogen, oxygen, nitrogen and a trace amount of zinc; exhibiting characteristic absorption peaks in the infrared region of the spectrum, when cast as a film on a silver chloride plate at the following frequencies expressed in reciprocal centimeters: 1616, 1543, 1517, 1463, 1400, 1367, 1233, 1191, 1106, 996, 977, 845 and 805; and formed by exposing to light in the presence of an oxygen source, a reactant mixture comprising: 2,2',4,4'-tetrahydroxybenzophenone, ammonium hydroxide and a trace amount of zinc.

65. A photo-product composition suitable for reducing electromagnetic radiation in the infrared and ultraviolet range, containing the elements carbon, hydrogen, nitrogen, oxygen and copper; exhibiting characteristic absorption peaks in the infrared region of the spectrum, when cast as a film on a silver chloride plate at the following frequencies expressed in reciprocal centimeters: 1734, 1617, 1377, 1234, 1161, 1125, and 1114; and formed by exposing to light in the presence of an oxygen source, a reactant mixture comprising: 2,2',4,4'-tetrahydroxybenzophenone, triethanolamine and copper cation.

66. A photo-product composition suitable for reducing electromagnetic radiation in the infrared and ultraviolent range, containing the elements carbon, hydrogen, nitrogen, oxygen and nickel; exhibiting characteristic absorption peaks in the infrared region of the spectrum, when cast as a film on a silver chloride plate, at the following frequencies expressed in reciprocal centimeters: 1747, 1608, 1581, 1440, 1266, 1226, 1153, 1120, 1097, 972, 875 and 751; and formed by exposing to light in the presence of an oxygen source a reactant mixture comprising: 2,2',4,4'-tetrahydroxybenzophenone, triethanolamine, ammonium hydroxide and nickel cation.

67. The processes of claims 3, 7, 15 or 26, further comprising contacting iodine.

* * * * *